United States Patent [19]

Johnson

[11] Patent Number: 4,576,737

[45] Date of Patent: Mar. 18, 1986

[54] ENCAPSULATION OF VOLATILE LIQUIDS

[75] Inventor: Richard S. Johnson, Wirral, England

[73] Assignee: Internationale Octrooi Maatschappij "Octropa" B.V., Rotterdam, Netherlands

[21] Appl. No.: 620,813

[22] Filed: Jun. 15, 1984

Related U.S. Application Data

[63] Continuation of Ser. No. 396,373, Jul. 8, 1982, abandoned.

[30] Foreign Application Priority Data

Jul. 21, 1981 [GB] United Kingdom ............... 8122414

[51] Int. Cl.⁴ ............................................. A01K 7/46
[52] U.S. Cl. ........................... 252/522 A; 252/174.11
[58] Field of Search .................................. 252/522 A

[56] References Cited

U.S. PATENT DOCUMENTS

| | | | |
|---|---|---|---|
| 1,155,977 | 10/1915 | Vernon | 426/453 X |
| 3,493,388 | 2/1970 | Hair | 426/453 X |
| 3,615,669 | 10/1971 | Hair et al. | 426/453 |
| 3,903,295 | 9/1975 | Palmer | 426/289 |
| 3,917,858 | 11/1975 | Bos | 426/453 X |
| 3,989,852 | 11/1976 | Palmer | 426/289 |
| 4,339,356 | 7/1982 | Whyte | 252/522 A |

FOREIGN PATENT DOCUMENTS 2028093 3/1980 United Kingdom .

OTHER PUBLICATIONS

Aretander, Perfume and Flavor Chemicals, vol. I, 1969, publ. by the author, Montclair, N.J., Monograph No. 3.

Primary Examiner—Anton H. Sutto
Attorney, Agent, or Firm—Cushman, Darby & Cushman

[57] ABSTRACT

This invention provides a process for the encapsulation of volatile liquids which can be natural or synthetic flavoring oils or perfumes in carriers, which are soluble in water. The encapsulates provided by this invention are prepared by spraying an emulsion comprising the carrier solution and the volatile liquid onto particles in a fluidized bed. The invention also provides detergent compositions and foodstuffs containing encapsulates of perfumes and flavors respectively.

5 Claims, No Drawings

ENCAPSULATION OF VOLATILE LIQUIDS

This is a continuation of application Ser. No. 396,373, filed July 8, 1982, now abandoned.

TECHNICAL FIELD

This invention relates to the encapsulation of volatile liquids. More particularly, the invention is concerned with the preparation of encapsulates of volatile liquids which are of an adequate size for their particular end-use. Such uses can include their introduction into various powdered compositions where, due to their size, they do not suffer segregation problems in relation to the rest of the composition. Likewise, they can be chosen to be of such a size that they do not reduce the flow properties of powdered compositions into which they are incorporated.

BACKGROUND ART

It has previously been proposed to prepare encapsulates of volatile liquids such as volatile natural or synthetic flavouring oils and perfumes in various carrier materials such as starch and dextrin derivatives by spray-drying emulsions containing the carrier material and volatile liquids (see, for example, U.S. Pat. No. 3,159,585).

However, in any spray-drying equipment, the particle size of the product from the spray-drying tower is thought to be related to the possible residence time of the droplets in the tower and of the ability of the particles to agglomerate and if large particles are required, a large tower must be used, which will inherently mean the production of large quantities of encapsulate material. In addition the viscosity characteristics of some carrier materials in emulsion or solution form can cause problems in atomisation in spray-drying towers.

Attempts have been made to obtain larger particles by the agglomeration of spray-dried particles in an agglomerator. However, when using a pan granulator or fluidised bed agglomeration to increase the size of spray-dried particles containing a volatile liquid, significant losses of that liquid are found to occur either during the agglomeration process or in subsequent storage, probably as a result of changes in the particle structure and their effect on its retention of the volatile liquid.

For various uses in the flavour and perfumery field, relatively small quantities of very specialised encapsulates are required and it is desirable that these encapsulates are of a particle size greater than that which can be achieved using small pilot plant spray-drying towers.

For example, it is desirable to introduce into fabric detergent washing powders encapsulates containing perfumes and it is difficult, using normal, small spray-drying equipment, to produce such encapsulate particles greater than 100 microns diameter. Ideally, for use in a fabric detergent powder, an encapsulate would be of the order of 500 microns diameter and such particles cannot be produced except in very large spray-drying towers of the size used in producing the detergent powder itself.

Similar criteria are involved in producing flavour-containing encapsulate particles for use in the foods industry and the present invention provides a process for the production of encapsulates of substantially greater size than those which can be made in small spray-drying towers which do not generate powder flow problems and which can readily be re-dissolved in, for example, water, without lumping or clustering together and so slowing down their solution.

SUMMARY OF THE INVENTION

Accordingly, the present invention provides a process for the encapsulation of a volatile liquid in which an emulsion of the volatile liquid in a solution of a carrier material is agglomerated in a fluidised bed by spraying the emulsion onto particles fluidised in the bed.

The volatile liquid used in this invention may be a flavouring oil or a perfume blend. It will be understood that such volatile liquids can contain, in solution, the usual gums, resins and vegetable and animal extracts normally used in the flavour and perfumery industries. It has been surprisingly found that even the very volatile "top notes" of perfumes can usefully be encapsulated using this process. This is particularly surprising, since in a paper read at the 2nd International Conference on Powder Technology (Powtech Conference) in 1975 in England, in a paper entitled "Fluidised Bed Processing of Bulk Solids" by E. J. Simon of Aeromatic Limited, Muttenz, Switzerland, the manufacturers of one fluidised bed system suggested that "The big advantage of coating in the fluid bed is that the solvents being used are immediately vapourised in the hot air stream, they cannot penetrate into the kernels and unexpected side-effects can be easily avoided."

It is not fully understood why this benefit has now been found in this equipment, but it may be related to the selection of the carrier material.

Suitable carrier materials for use in this invention include modified starches, such as dextrinised, acid-thinned and oxidised starches and maltodextrin. A preferred carrier is a dextrinised starch containing controlled amounts of hydrophobic side groups sold by Laing-National Limited in the United Kingdom, under the Trade Name "Capsul". Other suitable carrier materials, again, depending on the end use of the encapsulate, include gums such as gum-acacia and gelatins.

In general, it is desirable to use, as the carrier material, a material of adequate water solubility, such that a solution of at least 25% by weight solids can be readily achieved, preferably at least 35% by weight solids in water. It is also desirable that the flow characteristics of the aqueous solution are such that it can readily be sprayed.

Using the process provided by this invention it is possible to obtain a volatile liquid content in the carrier exceeding 30% by weight with a retention of over 90%.

A further important benefit arising from this process is that when the volatile liquid was a perfume, experienced perfumers were satisfied that the odour characteristics of the encapsulated perfume had not changed significantly from those of the original perfume.

The carrier concentration in water is conveniently in the range 30–50% by weight and the volatile liquid content in the emulsion is up to 50% by weight.

The fluidised bed apparatus for use in this process can be selected from those of various manufacturers, including Aeromatic AG of Muttenz in Switzerland and "Strea-1" laboratory agglomerator, also supplied by Aeromatic AG. Other useful agglomerators are supplied by the Calmic Division of William Boulton of Burslem, England.

The process may be carried out by spraying an emulsion of volatile liquid and a suitable carrier material in water into the fluidised bed agglomerator, which has previously been charged with a small quantity of a particulate carrier material or, preferably, with a sample of small encapsulates containing the volatile liquid to be employed in the bulk preparation.

The particles onto which the emulsion is sprayed can also be particulate material selected from edible materials such as powdered tea and ground spices or herbs.

The emulsion containing the volatile liquid coats the particulate material fluidised by the passage of air through the bed and causes some agglomeration of the particles and a build-up of the components of the emulsion including the volatile liquid. Since the residence time in the fluidised bed is controllable, the spraying of the emulsion may be continued until the required particle size of encapsulate has been obtained.

In commercial practice, it is desirable to run the process as a continuous one, using equipment of appropriate size for the production required. Such continuous running tends to ensure the maximum uniformity of product. To achieve this, careful control of input spray rate, fluidisation air-flow rate and its temperature must be exercised.

Furthermore, since the residence time is not critical, the equipment used for spraying in the emulsion onto the bed may be chosen to cover a wider range of viscosity and flow characteristics than is normally available in a spray-drying tower.

DETAILED DESCRIPTION

Details of actual experimental runs and the experimental conditions under which the agglomerator was used are set out in the following example.

EXAMPLE 1

This example describes the preparation of an encapsulate containing a nominal 30% w/w of a volatile perfume, a "top note" composition in a "Strea-1" laboratory agglomerator using corn starch as the initial support material.

Preparation of Emulsion 400 g of Capsul, a partially dextrinised chemically modified starch available from Laing-National Limited, was dissolved with agitation in 600 g of water held at 70-80° C. over a period of 20 minutes. This solution was then cooled and 250 g of a perfume "top note" composition (LP 843) was added, the mixture being vigorously agitated by means of a "Silverson" high-speed homogeniser. As a result the perfume was completely emulsified within the aqueous phase, the emulsion being stable for at least 24 hours.

Encapsulation 100 g of corn starch of particle size of about 20 microns was introduced in to the chamber of a "Strea-1" laboratory agglomerator (suitable for production of 1 Kg of product) and the chamber, fitted with filters and spray-nozzle, was placed in position on the machine. The corn starch was then fluidised with air heated to an inlet temperature of 80°-100° C. The degree of fluidisation could be controlled by varying the air flow rate and typically was adjusted so that the maximum lift of the corn starch particles within the chamber was below the position of the spray-nozzle. The emulsion was then pumped into the agglomerator by means of a Watson-Marlow Limited peristaltic pump and atomised at the two-fluid spray-nozzle, atomisation being effected by air at a pressure of between 1 and 2 bar. The rate of pumping of the emulsion was such that the bed remained free-flowing and fluidised throughout the preparation. Typically an emulsion flow rate of between 10 and 20 g/min was used. Fluidisation could also be controlled by adjustments to the fluidising air flow rate, some increase during the agglomeration generally being necessary. Typical machine parameters during a preparation are as follows:

| | | |
|---|---|---|
| Air inlet temp 100° C. | Filter resistance | 100 mm $H_2O$ |
| Air outlet temp 55° C. | Support plate resistance | 60 mm $H_2O$ |
| Fluidising air control setting 4 | Air flow rate | 50 $m^3$/hr |
| Atomiser nozzle air pressure 1.5 bar | | |

When all of the emulsion had been added fluidisation was continued for 2 to 3 minutes then stopped and the product discharged from the agglomerating chamber.

A typical product analysis was as follows:

Perfume content: 29.0%, i.e. 96.7% of nominal.

Overall yield: 97%.

Particle size distribution (Rosin-Rammler parameters, see Journal Institute of Fuel, Oct. 1933, pages 29-36): diameter=730μ n=2.1.

The "top note" formulation LP 843 consisted of:

| | % by weight |
|---|---|
| *Lavandin abrialis* | 40.0 |
| *globulus* | 10.0 |
| Rosemary Spanish | 5.0 |
| Ethyl amyl ketone | 2.0 |
| Hexyl acetate | 1.0 |
| Methyl hexyl ether | 0.5 |
| Turpentine | 5.0 |
| Linalyl acetate | 10.0 |
| Linalool | 10.0 |
| Ocimene | 3.0 |
| Camphor powder synthetic | 4.5 |
| Borneol | 1.5 |
| Terpinyl acetate | 7.5 |
| | 100.0 |

A sample of the encapsulate prepared according to this Example was placed in water and, when compared by a perfumer with the original LP 843 formulation, was considered to have produced an acceptably similar note.

EXAMPLE 2

This example describes the use of an Aeromatic AES 5.5 production size agglomerator having a nominal capacity of 15 Kg. The controls on this machine were essentially identical with those of the "Strea-1" described in Example 1.

10 Kg of emulsion containing a lemon perfume (AD 125) were prepared by the same procedure as described in Example 1. The support material comprised 2 Kg of agglomerate containing this lemon perfume prepared as described in Example 1 and contained 29.2% w/w of the perfume composition and had a particle size distribution defined by diameter=860μ n=2.3.

The support material was placed in the agglomerator and fluidised and the emulsion sprayed in via a "Schlick" two fluid nozzle operated at 2.5 bar air pressure. The air inlet temperature was 95° C. The emulsion addition rate was intially 2.5 Kg/hr being progressively increased during the first half-hour to a maximum of 5.6 Kg/hr as the bed built up. After a period of just under 2 hours the agglomerating chamber was full and spraying of the emulsion was stopped. On discharge the total product was found to be 8.2 Kg, ie just over half the nominal machine capacity, and this represented an overall product yield of 97.4%. Product perfume content was 28.1% w/w and moisture content 3.1%. Particle size analysis gave diameter = 820μ n = 1.9, bulk density 0.38 g/cc.

A sample of the encapsulate prepared according to this Example was placed in water and, when compared by a perfumer with the original AD 125 formulation, was considered to have produced an acceptably similar note.

The perfume containing encapsulates provided by this invention can usefully be incorporated into detergent compositions and the perfume is protected against the action of various components of the detergent and also against humidity changes in storage.

Accordingly this invention also provides encapsulates made by the process of this invention. In addition, this invention provides a perfumed detergent composition comprising by weight:

(a) from 0.1% to 30% of a water-soluble organic surfactant;
(b) from 0.04% to 5% of encapsulate provided by this invention containing, as the volatile liquid, a perfume; and the remainder,
(c) detergency fillers and extenders.

EXAMPLE 3

Using the apparatus and carrier material of Example 1, a flavour encapsulate was made with 250 g of lemon oil (FIL 50 49300, supplied by PPF International Limited of Ashford Kent, England) in place of the perfume. This encapsulate was found to have an improved shelf-life, when compared with flavour granules prepared from spray-dried flavour powders using the same lemon oil, and a more attractive organoleptic reception when tasted by a test panel.

Accordingly, this invention also provides an edible composition comprising an edible base and an organoleptically effective amount of an encapsulate provided by this invention in which the volatile liquid is a flavour.

EXAMPLE 4

Using the apparatus and procedures of Example 1, rum-flavoured granules were prepared. Gum acacia was employed both as carrier and initial particulate charge for the fluidised bed. The emulsion of flavour and carrier comprised, by weight:
94.82 parts of 40% aqueous gum acacia solution
0.554 parts rum ether
0.741 parts vanalin
3.885 parts rum base reference 3683064 from PPF International Limited of Ashford, Kent, England.

The emulsion was sprayed onto the powdered gum acacia in the fluidised bed and the final product met a specification of less than 2% over 2 mm mesh and less than 2% less than 0.25 mm mesh.

The rum flavoured granules were incorporated into teabags and stored for 6 months. Beverages prepared from the stored and freshly-prepared granules and tea compared satisfactorily in the view of an organoleptic panel.

EXAMPLE 5

Example 4 was repeated using tea powder in place of the gum acacia powder as the initial particulate charge. A product very similar to that in Example 4 was obtained and it also had a satisfactory flavour after 6 months' storage.

I claim:

1. A process for providing a particulate composition comprising liquid perfume encapsulated in a carrier material which comprises preparing a sprayable emulsion of the perfume in a solution of the carrier material, spraying the perfume-containing emulsion into a fluidized bed of particles whereby the perfume encapsulated in carrier material is deposited on the fluidized particles, continuing the spraying of the emulsion into the fluidized bed until the fluidized particles have the desired amount of encapsulated perfume deposited thereon and thereafter collecting the fluidized particles with the perfume encapsulated thereon.

2. Perfume encapsulates prepared by a process as claimed in claim 1.

3. A process as claimed in claim 1 wherein the perfume composition is emulsified in an aqueous solution of a carrier selected from the group consisting of starches, gum-acacia and gelatins, the solution containing 30–50% by weight of said carrier material and the content of perfume in said emulsion being up to 50% by weight, and the emulsion is sprayed into a fluidized bed agglomerator charged with a small quantity of particulate carrier or small encapsulates containing the perfume and continuing to spray the emulsion and maintain the fluidized bed until the desired particle size for the encapsulates is obtained.

4. A process as claimed in claim 1, in which the carrier material is selected from modified starches, dextrinised starches, acid-thinned starches, oxidised starches, dextrinised starches containing controlled amounts of hydrophobic groups, gums, gum-acacia and gelatins.

5. A process as claimed in claim 1 in which the carrier material has a solubility sufficient to permit the preparation of solutions containing at least 35% solids which are sprayable.

* * * * *